United States Patent [19]

Streckel et al.

[11] Patent Number: 5,306,328
[45] Date of Patent: Apr. 26, 1994

[54] PROCESS FOR THE PREPARATION OF COPPER POWDER

[75] Inventors: Willi Streckel; Herbert Straussberger, both of Mehring/Öd; Bernd Pachaly, Burghausen, all of Fed. Rep. of Germany

[73] Assignee: Wacker Chemie GmbH, Munich, Fed. Rep. of Germany

[21] Appl. No.: 989,685

[22] Filed: Dec. 14, 1992

[30] Foreign Application Priority Data

Dec. 20, 1991 [DE] Fed. Rep. of Germany ....... 4142432

[51] Int. Cl.$^5$ .............................................. B22F 9/24
[52] U.S. Cl. ...................................... 75/353; 75/373; 502/345
[58] Field of Search ..................... 75/353, 372, 373; 502/345

[56] References Cited

U.S. PATENT DOCUMENTS

| 3,282,675 | 11/1966 | Parker | 75/373 |
| 4,218,387 | 8/1980 | Maas et al. | 502/345 |
| 4,758,352 | 6/1986 | Feldner et al. | 210/719 |

FOREIGN PATENT DOCUMENTS

| 897437 | 4/1972 | Canada | 75/373 |
| 0057383 | 8/1982 | European Pat. Off. . | |
| 0344324 | 12/1989 | European Pat. Off. . | |
| 2055966 | 5/1971 | France . | |
| 63-33584 | 2/1988 | Japan | 75/372 |
| 1311294 | 3/1973 | United Kingdom . | |

*Primary Examiner*—George Wyszomierski

[57] ABSTRACT

Finely divided copper powder suitable for the preparation of copper catalyst for the synthesis of methylchlorosilane is prepared by adding an aqueous copper salt solution to an aqueous suspension of iron powder. Copper salt solutions obtained as process residues from the synthesis of methylchlorosilane can be used in the process of this invention.

7 Claims, No Drawings

PROCESS FOR THE PREPARATION OF COPPER POWDER

The invention relates to a process for the preparation of copper powder from copper solutions by reverse cementation with iron powder.

BACKGROUND OF THE INVENTION

The copper catalyst required in the synthesis of methylchlorosilane from methyl chloride and silicon is used in the form of metallic copper such as cement copper, electrolytic copper or oxidic copper prepared from cement copper by pyrometallurgical processes, or copper compounds such as copper oxides, copper hydroxides or other copper salts, or as an alloying constituent of silicon. To improve their activity, stability and reactivity, the copper catalysts contain metals as activators, such as aluminum or zinc, or as promoters, such as tin, antimony or arsenic.

When the direct synthesis is carried out in fluid-bed reactors, fines of silicon and copper catalyst, contaminated with carbon particles and various metal compounds from minor constituents of the technical-grade silicon raw material, are discharged together with the reaction product, the crude silane mixture and unconverted methyl chloride, and are separated off in downstream separating units, e.g. cyclones. A reactor residue consisting of silicon, catalyst and metal halides from minor constituents of the technicalgrade silicon raw materials, and carbon particles, is also obtained and is discharged continuously or discontinuously from the fluid-bed reactors. Drying and filtration processes also result in the production of contaminated dusts of very fine particle size.

The only currently known processes for the recovery of copper from process residues are those where contaminated copper salts are obtained which can only be recycled into the catalyst preparation after expensive purification.

U.S. Pat. No. 4,758,352 (K. Feldner el al., published on Jul. 19, 1988 in the name of Bayer A. G., Leverkusen) describes a process for the treatment of high-boiling residues from the synthesis of methylchlorosilane where the residues are hydrolyzed with water or dilute hydrochloric acid and oxidized with oxygen. The $CuCl_2$-containing solution which is separated off is treated with NaOH and $SO_2$ to precipitate copper(I) oxide.

This copper(I) oxide has to be worked up in known manner, for example by dissolution in dilute sulfuric acid with a supply of air followed by cementation with scrap iron. A further purification of the resulting copper by melt refining and then by an electrolytic process is usually required if fresh catalyst for the synthesis of methylchlorosilane is to be prepared therefrom.

Copper is ductile and cannot be mechanically reduced to a powder with a suitable particle size and surface. If a copper powder is to be prepared which will be processed further to a pulverulent catalyst for the synthesis of methylchlorosilane, for example by oxidation or doping of the copper surface, it has to be prepared by special processes, such as atomization, from the melt.

Therefore, it is an object of the present invention to provide a simple process for the preparation of copper powder which can be utilized as a catalyst in the synthesis of methylchlorosilane. A further object of the present invention is to provide a process for the preparation of copper powder from the copper salt solutions obtained in the working-up of process residues from the synthesis of methylchlorosilane.

SUMMARY OF THE INVENTION

The foregoing objects and others which will become apparent from the following description are accomplished in accordance with this invention, generally speaking, by providing a process for the preparation of finely divided copper powder suitable for the preparation of a copper catalyst for the synthesis of methylchlorosilane, which comprises incorporating an aqueous copper salt solution into an aqueous suspension of iron powder.

DESCRIPTION OF THE INVENTION

The deposition of a metal from a solution by the addition of a less noble metal, which is higher in the electrochemical series than the metal to be precipitated and goes into solution instead of the more noble metal, is called cementation of the more noble metal. Conventionally, copper is cemented by the addition of iron powder to a copper salt solution. In the present invention, the copper powder is prepared via reverse cementation.

The concentration of the copper salt solution is preferably between at least 0.2% by weight and the saturation point. The copper salt solution is preferably added continuously in such a way that the copper ion concentration remains constant and does not become too high. Vigorous mixing is also advantageous.

The copper powder prepared according to the invention can be partially oxidized after washing and drying and can be used as a highly active catalyst in the direct synthesis of methylchlorosilanes, if appropriate, after doping with activators or promoters. The necessary fineness of the copper is achieved not by physical or mechanical processes but by the process of this invention. A disagglomerating treatment in a mill is all that may be required.

Because of its low content of troublesome impurities such as lead, zinc, tin and titanium, the copper powder prepared according to this invention is also very suitable for processing to copper catalysts consisting of copper salts or for alloying the silicon used in the synthesis of methylchlorosilane.

The iron required in the process of this invention must be in powder form because a high reaction rate is necessary for the formation of the finely divided copper. Particularly good results are achieved when the average particle size of the iron powder is 0.1 to 100 $\mu$m. It is preferable to use sponge iron, which is obtained by the reduction of iron oxide in the solid state and has a particularly high porosity.

The pH in the aqueous suspension of iron powder is preferably below 3 so that no precipitates of iron hydroxide contaminate the copper powder. If the pH is too low, the iron powder is dissolved too rapidly. The best results are obtained when the pH of the suspension is 0.5 to 2.5.

The process of this invention can be carried out over the entire temperature range in which the aqueous suspension can be prepared at the appropriate pressure. However, the quality of the copper powder can best be controlled when the temperature of the suspension is 10 to 90° C.

By maintaining the preferred ranges for the particle size of the iron powder, the pH and the temperature, and by adding the copper salt solution uniformly, it is possible to keep the average particle size of the copper powder within the preferred range of from 0.5 to 50 μm. This is in fact the optimal particle size for a pulverulent copper catalyst for the synthesis of methylchlorosilane.

Copper salt solutions of diverse origins can be used in the process of this invention. Examples of suitable copper salt solutions are copper(II) chloride etching solution from the manufacture of printed circuit boards, or electrolytic copper wastes dissolved by mineral acids.

If the copper salt solution is obtained from process residues from the synthesis of methylchlorosilane, the process residues are worked up with mineral acid, if appropriate, with the addition of oxidizing agents, for example such as described in U.S. Pat. No. 4,758,352. The process residues are especially solid residues preferably containing less than 1% by weight of silanes. The process residues are preferably suspended with water, whereby dilute hydrochloric acid is formed. A mineral acid, such as hydrochloric acid, nitric acid or sulfuric acid, is then added, the presence of an oxidizing agent, such as oxygen, chlorine, NaOCl or $H_2O_2$, being necessary in the case of hydrochloric acid and sulfuric acid. All the metals which conventionally occur in process residues from the synthesis of methylchlorosilane pass into solution; silicon and carbon remain undissolved.

It is particularly preferred to recover copper(II) chloride with hydrochloric acid and oxygen, which can be blown in as atmospheric oxygen or as the pure gas.

Before it is incorporated into the aqueous suspension of iron powder, the copper salt solution is preferably treated with a flocculating agent and then filtered in order to separate off insoluble impurities such as fine carbon particles. It is preferred that synthetic, soluble, non-ionic flocculating agents or cationic flocculating agents be used.

The filter residue must be substantially free from elutable toxic metal compounds so that it can be dumped in accordance with the regulations or used for example as a raw material for high-temperature ceramics or, after oxidation, as an additive for mineral building materials. The elutable constituents of the filter residue can be kept to a minimum by washing with phosphoric acid or a basic aqueous solution. Bases which are preferably used are NaOH, KOH and Ca(OH)$_2$, especially NaOH. The filter residues treated with a basic aqueous solution comply with the legal requirements of the waste disposal regulations in respect of their elution values for copper and zinc.

The filtrate of the reverse cementation is a solution containing predominantly iron salt, which can be re-used. If the filtrate consists of iron chloride solution, this can be used for example as a flocculating agent in wastewater treatment plants.

In the synthesis of methylchlorosilane, the process of this invention makes it possible to recover almost all the copper used as catalyst, and permits a substantially closed copper circuit. Small copper losses which are unavoidable in the synthesis of methylchlorosilane can easily be made up by adding copper-containing aqueous solutions, such as the above-mentioned waste products from industrial processes, to the above-described aqueous suspension of the process residues.

In the following Examples, unless otherwise specified, (a) all amounts are by weight;
(b) all pressures are 0.10 MPa (abs.) and
(c) all temperatures are 20° C.

STEP 1

Suspending of the Process Residues from the Synthesis of Methylchlorosilane

About 500 g of a mixture containing reactor residues, cyclone dust and dryer dust from the filtration of crude silane were added to 1000 ml of water, with stirring. This suspending process was carried out under an inert gas, e.g., nitrogen, because the process residues can be pyrophoric. The elemental composition of this process residue was:

17.0% copper
4.2% iron
1.0% zinc
1.7% aluminum
0.9% calcium
0.4% titanium
Remainder: silicon, hydrocarbon and oxygen.

STEP 2

Dissolution of the Process Residues

About 300 l/hour of air were blown via a ceramic frit into the suspension of solids prepared according to Step 1, with stirring. The pH was kept at 1.5 by the continuous addition of 20% hydrochloric acid. The copper content of the solution increased to 57 g/l within 8 hours in which about 475 g of hydrochloric acid were consumed. The copper content of the undissolved solid component was below 0.5%.

STEP 3

Flocculation of the Solution Containing Solids

The solution obtained according to Step 2 contained undissolved fine particles of silicon and carbon. Filtration was only possible after flocculation, in which 0.5% of a 0.1% solution of a cationic flocculating agent (Sedipur CF 302 from BASF), was added with stirring. In a few seconds, the solid component agglomerated and could be filtered off without difficulty.

STEP 4

Filtration of the Flocculated Solution Containing Solids

A solution obtained according to Step 3 was filtered, it being necessary for the filter residue to be obtained in a form such that its eluate values complied with the legal requirements of the waste disposal regulations in respect of copper and zinc. This is achieved by passing 5 l of the solution containing solids through a Hoesch type MF62 filter press. After the filtrate had been stripped off, the residue was rinsed with 6 l of water, blown dry and then washed with 5 l of sodium hydroxide solution of pH 12. The filter residue obtained after pressing had a residual moisture content of 30%. An elution test according to DIN 38414 gave the following results in the eluate: pH 8.1, 0.05 mg/l of copper (limiting value according to waste disposal regulations: 10 mg/l) and 0.05 mg/l of zinc.

STEP 5

Reverse Cementation of the Copper and Preparation of the Catalyst

About 500 ml of water and 61 g of sponge iron powder with an average particle size of 60 to 70 μm were placed in a stirred vessel. About 1.5 l of a copper(II) chloride solution produced according to Step 4 (copper content about 45 g/l) were added over 30 minutes. The mixture was then stirred for 15 minutes. The cement copper was separated from the iron chloride solution by suction filtration. After the copper powder had been washed with 2 l of water and the water removed under suction, it was dried and oxidized at 170° C. in a circulating-air drying cabinet for 3 hours. The dried material was disagglomerated in an air-jet mill and separated from fractions over 25 μm by sizing. After doping, the copper catalyst obtained was reusable for the synthesis of methylchlorosilane. Yield of copper: 99%.

STEP 6

Synthesis of Methylchlorosilane with the Copper Catalyst

About 120 g of silicon powder having a particle size of 70–250 μm, mixed with a catalyst mixture consisting of 6 g of the copper catalyst prepared in Step 5, 2 g of zinc chloride and 6 mg of tin powder, were placed in a laboratory fluid-bed reactor equipped with heating coil, gas distribution frit, distillation bridge with brine cooling, and receiver flask. After heating to 350° C., 40 l/hour of methyl chloride were introduced. Methylchlorosilanes began to form after an induction time of 15 minutes. After an additional 107 minutes, 87 g of methylchlorosilane were present in the receiver flask. GC analysis of the reaction product showed 80.6% of $Me_2SiCl_2$, 6.5% of $MeSiCl_3$, 1.8% of $Me_3SiCl$, 8.5% of high-boiling components and 2.6% of low-boiling components.

What is claimed is:

1. A process for preparing finely divided copper powder suitable for the preparation of copper catalyst for the synthesis of methylchlorosilane, which comprises adding a flocculating agent to an aqueous copper salt solution obtained by treating a process residue from the synthesis of methylchlorosilane with mineral acid, with the proviso that an oxidizing agent is present when the mineral acid is hydrochloric acid or sulfuric acid, filtering the aqueous copper salt solution and then adding the filtered aqueous copper salt solution into an aqueous suspension of iron powder.

2. The process of claim 1, wherein the average particle size of the iron powder is 0.1 to 100 μm.

3. The process of claim 1, wherein the pH of the suspension is 0.5 to 2.5.

4. The process of claim 1, wherein the temperature of the suspension is 10° to 90° C.

5. The process of claim 1, wherein the average particle size of the copper powder is 0.5 to 50 μm.

6. The process of claim 1, wherein the mineral acid is hydrochloric acid, the oxidizing agent is oxygen, and the aqueous copper salt solution comprises copper (II) chloride.

7. The process of claim 1, further including a step of washing the filter residue with a basic aqueous solution.

* * * * *